United States Patent [19]

Jung et al.

[11] Patent Number: 5,760,263
[45] Date of Patent: Jun. 2, 1998

[54] ALKYLFERROCENES CONTAINING CHLOROSILYL GROUPS AND THEIR PREPARATION METHODS

[75] Inventors: Il Nam Jung; Sam Young Ahn, both of Seoul; Bok Ryul Yoo, Kyungki-do; Joon Soo Han, Kwangjin-ku, all of Rep. of Korea

[73] Assignee: Korea Institute of Science and Technology, Seoul, Rep. of Korea

[21] Appl. No.: 880,492

[22] Filed: Jun. 23, 1997

[30] Foreign Application Priority Data

Jun. 25, 1996 [KR] Rep. of Korea ............... 23548/1996
Apr. 7, 1997 [KR] Rep. of Korea ............... 12730/1997

[51] Int. Cl.$^6$ .................. C07F 17/02; C07F 15/02
[52] U.S. Cl. .................. 556/11; 556/12; 556/143; 526/943
[58] Field of Search .................. 556/11, 12, 143

[56] References Cited

U.S. PATENT DOCUMENTS

3,321,501 5/1967 Wilkus et al. ............... 260/429
3,414,597 12/1968 Wilkus et al. ............... 260/429
3,759,967 9/1973 Sollott et al. ............... 260/439 CY

OTHER PUBLICATIONS

M. Rosenblum, et al., "The Chemistry and Structure of Fereocene. VIII. Interannular Resonance and the Mechanism of Electrophilic Substitution", J. AM. Chem. Soc., vol. 85, May 20, 1963, pp. 1450–1458.

G.A. Olah, "Friedel–Crafts and Related Reactions", Interscience Publishers, vol. IV, 1965, p. 128.

V.P. Tverdokhlebov, et al., "Alkylation of Ferrocene. I. Reaction of Ferrocene with Ethylenechlorohydrin and Dibromoethane", Chem. Abstr., vol. 97, 216408q, 1982, p. 875.

A.N Nesmeyanov, et al., "Alkylation of Ferrocene", Chem. Abstr., vol. 51, No. 10, 1957, 5057h.

A.N Nesmeyanov, et al., "Reaction of Ferrocene with Olefins", Chemical Abstracts, vol. 52, 1958, 12852c.

M. Rosenblum, et al., "Protonation of Ferrocene by Strong Acids", J. AM. Chem. Soc., vol. 81, Oct. 20, 1959, pp. 5517–5518.

W.E Watts, "The Organic Chemistry of Metal–coordinated Cyclopentadienyl and Arene Ligands", Comprehensive Organometallic Chemistry, vol. 8, 1982 p. 1017.

N.S. Nametkin, et al., "Alkylation of Aromatic Compounds by Allylsilane Chlorides" Chem. Abstr., vol. 66, No. 29, 65564u, 1967, p. 6177.

S.H. Yeon, et al., "Problems and Solutions Involved in Direct Synthesis of Allylchlorosilanes", Organometallics, vol. 12, No. 12, 1993, pp. 4887–4891.

B.W. Lee, et al., "Hydrosilylation of Olefins with Allyldichlorosilane: A Convenient Route to Allyl Group Containing Organodichlorosilanes" Main Group Chemistry, vol. 1, 1995, pp. 53–60.

B.W. Lee, et al., "Friedel–Crafts Alkylation of Substituted Benzenes by Allyldichlorosilane" Organometallics, vol. 13, No. 4, 1994, pp. 1312–1316.

*Primary Examiner*—Porfirio Nazario-Gonzalez
*Attorney, Agent, or Firm*—Oblon, Spivak, McClelland, Maier & Neustadt, P.C.

[57] ABSTRACT

The present invention relates to ferrocenes containing silylalkyl groups, represented by formula(I) and their preparation methods by reacting ferrocene with allylchlorosilanes represented by formula(II) in the presence of Lewis acid catalysts such as aluminum chloride:

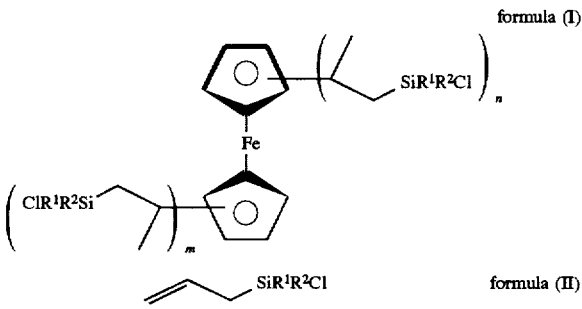

formula (I)

formula (II)

wherein $R^1$ represents hydrogen, $C_1$–$C_{12}$ alkyl, or $C_1$–$C_{12}$ alkyl containing phenyl group; $R^2$ represents chloro, $C_1$–$C_{12}$ alkyl, or $C_1$–$C_{12}$ alkyl containing phenyl group; and n and m are 0, 1 or 2, respectively, and at least one of n and m is not zero.

4 Claims, No Drawings

ALKYLFERROCENES CONTAINING CHLOROSILYL GROUPS AND THEIR PREPARATION METHODS

FIELD OF THE INVENTION

The present invention relates to ferrocenes containing silylalkyl groups and preparation methods thereof.

BACKGROUND OF THE INVENTION

Ferrocene behaves in many respects like an electron-rich aromatic compound, which is activated by an electrophilic reaction. Thus, Friedel-Crafts type acylation of ferrocene with acyl halides leads to an acylferrocenes. Ferrocene is $10^6$ times more reactive compared to benzene in acylation and yields more than 80%( Rosenblum, M., Santer, J. O. Howells, W. G., J. Am. Chem. Soc., 85, 1450 (1963). However, the Friedel-Crafts type alkylation of ferrocene with respect to reactivity and yields, of alkyl halides or olefins is different from that of benzene. The yields of alkylferrocenes are often very low and the separations of polysubstituted byproducts are often tedious (Olah, G. A., Friedel-Crafts and related Reations, Vol. IV, Interscience Publishers, 1956, p128; V. P. Tverdokhlebov, B. V. Polyakov, I. V. Tselinskii, L. I. Golubena, Zhurnal Obshchei Khimii, vol. 52, 2032 (1982).

Nesmeyanov and Kochetkova first reported the Friedel-Crafts type alkylation of ferrocene to produce alkylferrocenes [Nesmeyanov, A. N.; Kochetkova, N. S., Dokl. Akad. Nauk S.S.S.R, 109, 543, (1956)]. They reacted ferrocene with ethyl bromide in the presence of an aluminum chloride catalyst to produce ethylferrocenes. The yield of the single alkylated product was only 4%, and the double alkylated 1,2-diethylferrocene and the triple alkylated triethylferrocene was 3.5%, respectively. They also reported the alkylation of ferrocene with olefin to produce alkylferrocenes. They also reacted ferrocene with ethylene in the presence of an aluminum chloride catalyst to produce ethylferrocene. The yield of ethylferrocene was 20.5% [Nesmeyanov, A. N.; Kochetkova, N. S., Izv. Akad. Nauk S.S.S.R., Otd. Khim, Nauk, 242, (1958).]

It was believed that the low yield in the alkylation of ferrocene with alkyl halide or olefin was due to the easy oxidation of ferrocene and the formation of ferrocene/aluminum chloride complex which is a greenish adduct of $(C_{10}H_{10}Fe.HAlCl_4)_n$. [Rosenbaum, M.; Santer, J. O., J. Am. Chem. Soc, 81, 5517(1959)]. If the complex was formed, the catalytic activity of aluminum chloride would be reduced and the complex would not react with the alkyl halide or olefin. Therefore, the alkylated ferrocenes are usually prepared in multisteps by reducing the acylferrocenes which are easily prepared by the acylation of ferrocene (W. E. Watts in Wilkinson, G.; Stone, F. G. A.; Abel, E. W., Comprehensive Organometallic Chemistry, Vol. 8, Pergamon Press, 1982, p. 1017).

Nametkin and his co-workers reported the Friedel-Crafts type addition of allylchlorosilanes to mono substituted benzenes to produce 3-phenyl-1-silabutane [Nametkin, N. S.; Vdovin, V. M.; et al., Izv. Akad. Nauk SSSR, Ser. Khim, 11, 1998, (1966)]. They reacted allyltrichlorosilane, allyldichlorosilane, allylmethyldichlorosilane, or allyltrimethylsilane with benzene, chlorobenzene, bromobenzene or benzyltrichlorosilane in the presence of aluminum chloride to produce 2-phenylpropylsilanes. The yield of 2-(phenyl) propyldichlorosilane from the reaction of allyldichlorosilane with benzene was 60%. However, the Friedel-Crafts type alkylation of ferrocene with silyl group containing olefins has never been reported.

The present inventors reported a preparation method of allylchlorosilanes by directly reacting silicon metal simultaneously with allyl chloride and hydrogen chloride in the presence of a copper catalyst at a temperature of from 220° C. to 350° C. Allyldichlorosilane was obtained as the major product indicating that one mole of each reactant reacted with the same silicon atom. When a sufficient amount of hydrogen chloride was added, diallyidichlorosilane was not formed. This eliminated the polymerization problem involved with direct synthesis [Yeon, S. H.; Lee, B. W.; Kim, S. I.; Jung, I. N. Organometallics, 12, 4887, (1993)]. Recently, the present inventors reported a hydrosilylation reaction of allyidichlorosilane with olefins containing a various alkyl group with or without a phenyl group [Lee, B. W.; Yoo, B. R.; Yeon, S. H.; Lee, K. B.; Jung, I. N. Main Group Chem., 1, 53, (1995)]. They also reported the preparation method of (2-arylpropyl)dichlorosilanes by the Friedel-Crafts alkylation of various substituted aromatic compounds with allyidichlorosilane in the presence of Lewis acid catalysts. The yields were in the range of 60–80%. [Jung, I. N.; Lee, B. W.; Yoo, B. Y.; Kim, S. I., Organometallics, 13, 1312, (1994)].

SUMMARY OF THE INVENTION

The present invention relates to ferrocenes containing silylalkyl groups represented by the formula (I) and preparation methods thereof by reacting ferrocene with allylchlorosilanes represented by the formula(II) in the presence of Lewis acid catalysts such as aluminum chloride:

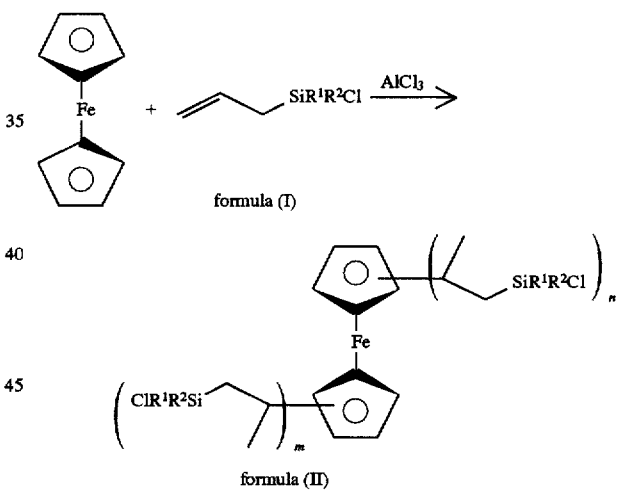

formula (I)

formula (II)

wherein $R^1$ represents hydrogen, $C_1$–$C_{12}$ alkyl, or $C_1$–$C_{12}$ alkyl containing a phenyl group; $R^2$ represents chloro, $C_1$–$C_{12}$ alkyl, or $C_1$–$C_{12}$ alkyl containing a phenyl group; and n and m are 0, 1 or 2, respectively, and at least one of n and m is not zero.

DETAILED DESCRIPTION OF THE INVENTION

The preparation of alkylferrocenes containing chlorosilyl groups according to the present invention can be run in standard laboratory glasswares and commercial equipments under inert atmosphere, with units for external heating and cooling, stirring, and incremental addition of silanes. The reaction can be carried out in most nonaromatic or nonprotic solvents, such as didhloromethane. In a typical preparation, ferrocene and allylsilane (represented by the formula I) are placed in the reactor under inert atmosphere. Aluminum chloride is the best catalyst which can be used alone or with the addition of another Lewis acid, such as: chlorides of zinc, boron, iron, tin, titanium and antimony. A solution of the aluminum chloride in dichloromethane is then slowly added to the reactants in the reactor with stirring at a reaction temperature between 0° C. and 50° C. When the aluminum chloride catalyst is added to ferrocene at the beginning of the reaction, the poor yield is probably due to the aluminum chloride/ferrocene complex. After the additions are completed, the solution may be stirred for a certain period of time to complete the alkylation, and then the products may be fractionally distilled at atmospheric pressure or under a vacuum.

The alkylation not only gives the monoalkylated formula product, but also the di-, tri-alkylated products of formula I. For example, the yields of the monoalkylated product and the dialkylated product vary depending upon the amount of allylchlorosilanes (formula (II)) added with respective to the ferrocene. The more allylchlorosilane added, the more of the dialkylated products are produced. The dialkylation produces several stereoisomers which have alkyl groups on the same cyclopentadiene ring and on different rings as well. Since the dialkylated products have two chiral centers, it is possible that the stereoisomers can be two diastereoisomers.

The invention will be further illustrated by the following examples, but not limited to the examples given.

EXAMPLE 1

Preparation of (3-chloro-1,3-dimethyl-3-silabutyl) ferrocene and bis(3-chloro-1,3-dimethyl-3-silabutyl)f To a 100 mL, three-necked, flame dried, round bottomed flask equipped with a mechanical stirrer, a reflux condenser and a rubber stopper having a small teflon tube connected to a syringe pump, 0.30 g (1.61 mmol) of ferrocene and 0.46 mL(3.15 mmol) of allyldimethylchlorosilane was placed under dry nitrogen atmospheric pressure. To the reaction mixture (with stirring) 20.0 mL of aluminum chloride suspended in methylene chloride [containing 0.04 g (0.3 mmol) of aluminum chloride] was slowly added dropwise, via a syringe pump at a rate of 0.3 mL/min. After the addition was completed, the solution was stirred for 2 hrs in ordered to complete the alkylation. The solvent was distilled off at atmospheric pressure and the products were then extracted with 20.0 mL of hexane. The reaction products were distilled under a vacuum at 200° C. and at 0.5 torr, and produced 0.07 g of nonreacted ferrocene, 0.26 g of a monoalkylated product (I) (yield; 66% based on the reacted ferrocene, bp; 142°–150° C./0.5 torr). The remaining products were vacuum distilled at 300° C. at 0.5 torr. The dialkylated product (II) as a mixture of four isomeric products produced 0.08 g (yield; 13%, bp;170°–175° C./0.5 torr).

(3-Chloro-1,3-dimethyl-3-silabutyl)ferrocene(I);

$^1$H NMR (ppm, CDCl$_3$) 0.43, 0.44(s, 3H, SiCH$_3$), 1.05–1.13(dd, 1H, CH$_a$H$_b$), 1.27–1.29(dd, 1H, CH$_a$,H$_b$), 1.33–1.35(d, 3H, CCH$_3$)2.77–2.85(m, 1H, CHMe), 4.09(s, 44.16(s, 5H, Cp)

Bis(3-chloro-1,3-dimethyl-3-silabutyl)ferrocene(II);

$^1$H NMR (ppm, CDCl$_3$) 0.42, 0.45(s, 12H, SiCH$_3$), 1.05–1.13(m, 4H, CH$_a$H$_b$) 1.27–1.30(d, 6H, CCH$_3$), 2.77–2.85(m, 2H, CHMe), 4.06, 4.11, 4.14(s,8H,Cp)

EXAMPLE 2

Alkylation of ferrocene with allyldimethylchlorosilane (1:4 ratio)

In the same apparatus and procedures as EXAMPLE 1 above, 0.30 g(1.61 mmol) of ferrocene was reacted with 0.92 mL(6.3 mmol) of allyldimethylchlorosilane under dry nitrogen atmospheric pressure for 2 hrs. After the addition of the catalyst solution, the reaction mixture was stirred for an additional 2 hrs to complete the alkylation. The solvent was distilled off at atmospheric pressure and the products were then extracted with 20.0 ml. of hexane. The reaction products were distilled under vacuum at 200° C. and at 0.5 torr, and produced 0.1 g of (3-chloro-1,3-dimethyl-3-silabutyl) ferrocene (yield; 20%). The remaining products were vacuum distilled at 300° C. and at 0.5 torr, and 0.55 g of bis(3-chloro-1,3-dimethyl-3-silabutyl)ferrocenes(yield; 38%) was obtained.

EXAMPLE 3

Preparation of (3,3-dichloro-1-methyl-3-silabutyl) ferrocene and bis(3,3-dichloro-1-methyl-3-silabutyl) ferrocene In the same apparatus and procedures as EXAMPLE 1, 0.60 g (3.22 mmol) of ferrocene was reacted with 1.00 g (6.44 mmol) of allylmethyldichlorosilane under dry nitrogen atmospheric pressure for 2 hrs. After the addition of the catalyst solution, the reaction mixture was stirred for 2 hrs to complete the alkylation. The solvent was distilled at atmospheric pressure and the products were then extracted with 20.0 mL of hexane. Vacuum distillation of the reaction products at 180° C. and at 0.5 torr, produced (3,3-dichloro-1-methyl-3-silabutyl)ferrocene [yield: 21% (based on the reacted ferrocene), bp:(104°–110° C./0.5 torr)]. By vacuum distillation of the remaining products at 300° C. and at 0.5 torr, bis(3,3-dichloro-1-methyl-3-silabutyl)ferrocene as a mixture of isomers(m=1, n=1, yield; 7%, bp; 165°–170° C./0.5 torr) was obtained.

$^1$H NMR (ppm, CDCl$_3$) 0.74(s, 3H, SiCH$_3$), 1.36–1.45 (dd, 1H, CH$_a$H$_a$Si), 1.40(d, 3H, $^3$J=6.9 Hz, CH$_3$), 1.55–1.62 (dd, 1H, CH$_a$CH$_a$Si), 2.91(m, 1H, CHMe), 4.12(s, 4H), C$_5$H$_4$), 4.17(s, 5H, Cp).

Bis(3,3-dichloro-1-methyl-3-silabutyl)ferrocene(m=1, n=1)

$^1$H NMR(ppm, CDCl$_3$) 0.73(s, 6H, 2×SiCH$_3$), 1.26–1.59 (m, 10H, 2×CH$_2$2.88–2.90(m, 2H, 2×CHCH$_3$), 4.07, 4.13, 4.16(s, 8H, Cp).

EXAMPLE 4

Preparation of (3,3-dichloro-1-methyl-3-silabutyl) ferrocene and bis(3,3-dichloro-1-methyl-3-silabutyl) ferrocene (1:4 ratio)

In the same apparatus and procedures as EXAMPLE 1, 0.60 g (3.22 mmol) of ferrocene was reacted with 2.0 g (12.88 mmol) of allylmethyldichlorosilane under the dry nitrogen atmospheric pressure for 2 hrs. After the addition of the catalyst solution, the reaction mixture was stirred for 2 hrs to complete the alkylation. The solvent was distilled off at atmospheric pressure and the products were then extracted with 20.0 mL of hexane. By vacuum distillation at 1000° C. and at 0.5 torr of the reaction products, (3,3-dichloro-1-methyl-3-silabutyl)ferrocene [yield: 9%(based on the reacted ferrocene)] was obtained. By vacuum distillation of the remaining products at 300° C. and at 0.5 torr, bis(3,3-dichloro-1-methyl-3-silabutyl)ferrocene as a mixture of isomers(yield; 35%) was obtained.

EXAMPLE 5

Preparation of (3-chloro-1,4,4-trimethyl-3-silapentyl) ferrocene

In the same apparatus and procedures as EXAMPLE 1, 0.60 g (3.22 mmol) of ferrocene was reacted with 1.05 g (6.44 mmol) of allyl-tert-butylchlorosilane under dry nitrogen atmospheric pressure for 2 hrs. After the addition of the catalyst solution, the reaction mixture was stirred for 2 hrs to complete the alkylation. The solvent was distilled off at atmospheric pressure and the products were then extracted with 20.0 ml of hexane. Vacuum distillation of the reaction products at 200° C. and at 0.5 torr produced (3-chloro-1,4,4-trimethyl-3-silapentyl)ferrocene [yield: 26% (based on the reacted ferrocene)].

(3-Chloro-1,4,4-trimethyl-3-silapentyl)ferrocene (m=0, n=1)

$^1$H NMR (ppm, CDCl$_3$) 1.01, 1.03(s, 9H, C(CH$_3$)$_3$), 1.29–1.40(m, 5H, CH$_a$H$_a$Si+CH$_3$CH), 2.84(m, 1H, CH), 4.09, 4.14(s,9H, Cp), 4.59, 4.48(d, 1H, SiH).

EXAMPLE 6

Preparation of (3,3-dichloro-1-methyl-3-silaoctyl) ferrocene

In the same apparatus and procedures as EXAMPLE 1, 0.60 g(3.22 mmol) of ferrocene was reacted with 1.45 g(6.44 mmol) of allyl-n-hexyldichlorosilane under the dry nitrogen atmospheric pressure for 2 hrs. After the addition of the catalyst solution, the reaction mixture was stirred for 2 hrs to complete the alkylation. The solvent was distilled off at atmospheric pressure and the products were then extracted with 20.0 mL of hexane. By vacuum distillation of the reaction products at 300° C. and at 0.5 torr, (3,3-dichloro-1-methyl-3-silaoctyl)ferrocene [yield: 26%(based on the reacted ferrocene), bp:(165–170° C./0.5 torr)] was obtained.

(3,3-Dichloro-1-methyl-3-silaoctyl)ferrocene $^1$HNMR(ppm, CDCl$_3$)0.92(t, 2H,SiCH$_2$), 1.03(tt, 2H, SiCH$_2$CH$_2$), 1.31–1.59(m 15H, SiCH$_2$CH$_2$C$_4$H$_9$, CH(CH$_3$)CH$_2$Si), 4.07, 4.16(s, 9H, Cp).

What is claimed is

1. A ferrocene containing silylalkyl groups represented by formula I

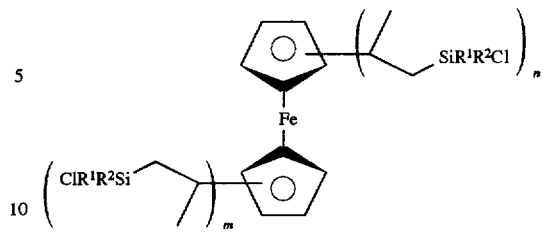

wherein $R^1$ represents hydrogen, $C_1$–$C_{12}$ alkyl, or $C_1$–$C_{12}$ alkyl containing phenyl group; $R^2$ represents chloro, $C_1$–$C_{12}$ alkyl, or $C_1$–$C_{12}$ alkyl containing phenyl group; and n and m are 0, 1 or 2, respectively, and at least one of n and m is not zero.

2. A method to prepare a ferrocene containing silylalkyl groups represented by formula I by reacting ferrocene with allylchlorosilanes represented by formula II in the presence of Lewis acid catalysts;

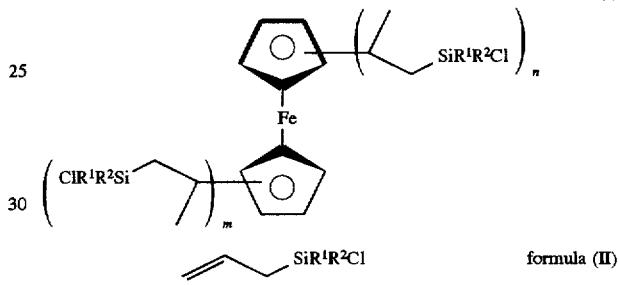

wherein $R^1$ represents hydrogen, $C_1$–$C_{12}$ alkyl, or $C_1$ $_R{}^2$ represents chloro, $C_1$–$C_{12}$ alkyl, or $C_1$–$C_{12}$ alkyl containing phenyl group; and n and m are 0, 1 or 2, respectively, and at least one of n and m is not zero.

3. The method according to claim 2 wherein the Lewis catalyst is aluminum chloride.

4. The method according to claim 3 wherein the amount of aluminum chloride is 0.5–20wt % of the allylchlorosilanes of formula II.

* * * * *